United States Patent [19]

Kawano et al.

[11] Patent Number: 4,877,874

[45] Date of Patent: Oct. 31, 1989

[54] PROCESS FOR PRODUCING N-AMINOHEXAMETHYLENEIMINE

[75] Inventors: Minoru Kawano; Katsumi Simizu; Eiji Isonaga; Shigeo Kurata, all of Ube, Japan

[73] Assignee: Ube Indrustries, Ltd., Ube, Japan

[21] Appl. No.: 54,315

[22] Filed: May 26, 1987

[30] Foreign Application Priority Data

Jun. 13, 1986 [JP] Japan .................. 61-136113

[51] Int. Cl.$^4$ ............................. C07D 295/22
[52] U.S. Cl. ............................ 540/606; 540/605
[58] Field of Search ..................... 540/605, 606

[56] References Cited

U.S. PATENT DOCUMENTS

| | | | |
|---|---|---|---|
| 3,583,979 | 6/1971 | Lorentz et al. | 260/239 B |
| 3,887,543 | 6/1975 | Nakanishi et al. | 260/239.3 B |
| 3,891,706 | 6/1975 | Wilcox | 260/569 |
| 3,976,753 | 8/1976 | Grant | 423/351 |

FOREIGN PATENT DOCUMENTS 128770 10/1981 Japan .

OTHER PUBLICATIONS

Nakamizo et al., *Chem. Abstracts*, vol. 107 (1987) 134623s.
Koga et al., *Tetrahedron Letters*, No. 15, pp. 1291–1294 (1978).
Somei et al. I *Chem. Pharm. Bull.*, vol. 26 (1978) pp. 2522–2534.
Somei et al., II *Tetrahedron Letters*, No. 5 (1974) pp. 461–2.
Hofer et al., *Synthesis* (6) 466–7 (1983).
Raap, Rintje *Canadian Journal of Chemistry*, vol 47 (19) 3677–81.
Gabriel Gever and Kenyon Hayes, pp. 813–818 (1949)–"Alkylhydrazines", Contribution from the Div. of Chem., Eaton Laboratories, Inc.

*Primary Examiner*—Glennon H. Hollrah
*Assistant Examiner*—Peter G. O'Sullivan
*Attorney, Agent, or Firm*—Frishauf, Holtz, Goodman & Woodward

[57] ABSTRACT

There is disclosed a process for producing N-aminohexamethyleneimine, which comprises allowing hexamethyleneimine to react with hydroxylamine-O-sulfonic acid in the presence of an aqueous solvent and an inorganic base.

18 Claims, No Drawings

PROCESS FOR PRODUCING N-AMINOHEXAMETHYLENEIMINE

BACKGROUND OF THE INVENTION

This invention relates to a process for producing N-aminohexamethyleneimine.

N-aminohexamethyleneimine is useful as an intermediate for pharmaceuticals and others, and above all it is a useful intermediate for Tolazamide (trade name) which is effective as the medicine for diabetes.

In the prior art, as a process for producing N-aminohexamethyleneimine, in U.S. Pat. No. 3,583,979, there is disclosed a process which comprises allowing hexamethyleneimine to react with sodium nitrite under acidic condition of hydrochloric acid to produce once N-nitrosohexamethyleneimine and then reducing this.

However, this process is cumbersome in operation since two steps are involved, and mixing of N-nitrosohexamethyleneimine formed as the intermediate into N-aminohexamethyleneimine cannot be avoided.

This N-nitrosohexamethyleneimine is strongly toxic, and therefore it is strongly desirable to have a process for production in which no N-nitrosohexamethyleneimine is formed.

SUMMARY OF THE INVENTION

An object of the present invention is to provide a novel process for producing N-aminohexamethyleneimine which responds to the demand in the technical field concerned as mentioned above and has overcome the drawbacks of the prior art process.

The present invention concerns a process for producing N-aminohexamethyleneimine which comprises allowing hexamethyleneimine to react with hydroxylamine-O-sulfonic acid (hereinafter abbreviated as HOS) in the presence of an aqueous solvent and an inorganic base.

DESCRIPTION OF THE PREFERRED EMBODIMENTS

According to the process of the present invention, N-aminohexamethyleneimine which is the desired product and unreacted hexamethyleneimine form a layer as an organic layer, while sulfate which is the by-product is separated into aqueous layer.

The reason why hexamethyleneimine is thus reacted in the presence of an aqueous solvent is because it is not particularly required to perform the operation for separating the by-product, since when the reaction mixture is left to stand after the reaction, the by-product of sulfate is separated into aqueous layer and the desired product forms an organic layer.

In this case, for making the loss of the desired product into the aqueous layer smaller, the proportion of water relative to pure HOS in the reaction system should be preferably 4.5 to 8 parts by weight of water quantity per 1 part by weight of pure HOS. If the water quantity is within the above range, the concentration of the aqueous hexamethyleneimine solution and the concentration of the mixture of HOS and water are not limited. If the water quantity is less than the above range, in addition to precipitation of sulfate, yield will be undesirably lowered.

As the inorganic base to be used in the present invention, there may be employed hydroxides of alkali metals, hydroxides of alkaline earth metals, etc.

Typical examples of hydroxides of alkali metals may include sodium hydroxide, potassium hydroxide and the like.

On the other hand, typical examples of hydroxides of alkaline earth metals may include magnesium hydroxide, calcium hydroxide, barium hydroxide and the like.

The amount of the base used may be considered to be required to be at least equivalent to by-produced sulfuric acid and sulfuric acid attached to HOS in the sense of preventing formation of salts with hexamethyleneimine and N-aminohexamethyleneimine, 1.0 to 3.0 equivalents, preferably 1.0 to 1.5 equivalents based on the theoretical amount.

The proportion of hexamethyleneimine relative to pure HOS in the present invention may be preferably 2 to 4 moles of hexamethyleneimine per 1 mole of pure HOS.

The method for injecting starting materials is not particularly limited, but it is preferred to carry out the reaction by mixing and stirring at the same time an aqueous solution of hexamethyleneimine with an aqueous solution of HOS and a base. Above all, it is particularly preferred in aspect of improvement of the reaction yield to carry out the reaction by injecting simultaneously an aqueous solution of HOS and a base into an aqueous solution of hexamethyleneimine.

The reaction of the present invention can be carried out at a temperature generally of 0° to 100 C., preferably of 10° to 50 ° C., within one hour.

By carrying out thus the reaction, N-aminohexamethyleneimine which is the desired product and unreacted hexamethyleneimine form a layer as an organic layer, and the sulfate which is the by-product is separated into aqueous layer.

After completion of the reaction, isolation of N-aminohexamethyleneimine formed in the organic layer separated can be done easily by employing suitably known operations such as concentration, distillation, etc.

In the process of the present invention, since no N nitrosohexamethyleneimine is formed during the reaction, in the thus isolated N-aminohexamethyleneimine, no toxic N-nitrosohexamethyleneimine is contained as in the prior art.

The effects of the present invention are as enumerated below.

(1) The present invention can be practiced in one step as contrasted to the prior art method, and besides can obtain N-aminohexamethyleneimine containing no N-notrosohexamethyleneimine at all.

(2) Separation of the by-produced sulfate from the desired product can be easily done.

(3) Excessive hexamethyleneimine can be simply recovered and reutilized as the starting material.

EXAMPLES

The present invention is described below by referring to Examples.

The yield of N-aminohexamethyleneimine in Examples is based on the moles of the reacted hexamethyleneimine.

EXAMPLE 1

To a mixture of 89.3 g (0.9 mole) of hexamethyleneimine and 35.1 g of water were injected at the same time a cooled mixture of 44.1 g (0.3 mole) of 77.09% by weight HOS (20 % by weight of sulfuric acid and 2 % by weight of hydroxylaminesulfate) and 79.2 g of water, and 105.6 g of 30% by weight sodium hydroxide (0.792 mole) at 30 to 35 ° C. under stirring, and after completion of injection the reaction was carried out at 30° C. under stirring for 30 minutes. After the reaction, the reaction mixture was subjected to phase separation at 30° C. into the organic phase and the aqeuous phase, and 150.7 g of the organic layer containing the desired product was obtained. As the result of GC analysis of the organic layer, the yield of N-aminohexamethyleneimine was found to be 81.7%.

EXAMPLE 2

To a mixture of 29.8 g (0.3 mole) of hexamethyleneimine and 6.8 g of water were injected at the same time a cooled mixture of 14.7 g (0.1 mole) of 77.09% by weight HOS (20% by weight of sulfuric acid and 2 % by weight of hydroxylamine sulfate) and 26.4 g of water, and 42.2 g of 30% by weight sodium hydroxide (0.317 mole) at 30° to 35° C. under stirring, and after completion of injection the reaction was carried out at 30° C. under stirring for 10 minutes. After the reaction, the reaction mixture was subjected to phase separation at 30° C. into the organic phase and the aqeuous phase, and 45.5 g of the organic layer containing the desired product was obtained. As the result of GC analysis of the organic layer, the yield of N-aminohexamethyleneimine was found to be 80.9%.

EXAMPLE 3

To a mixture of 29.8 g (0.3 mole) of hexamethyleneimine and 11.7 g of water were injected at the same time a cooled mixture of 14.7 g (0.1 mole) of 77.09% by weight HOS (20% by weight of sulfuric acid and 2% by weight of hydroxylamine sulfate) and 26.4 g of water, and 28.2 g of 30% by weight sodium hydroxide (0.212 mole) at 30° to 35° C. under stirring, and after completion of injection the reaction was carried out at 30° C. under stirring for 10 minutes. After the reaction, the reaction mixture was subjected to phase separation at 30° C. into the organic phase and the aqeuous phase, and 48.8 g of the organic layer containing the desired product was obtained. As the result of GC analysis of the organic layer, the yield of N-aminohexamethyleneimine was found to be 81.0%.

EXAMPLE 4

To 19.8 g (0.2 mole) of hexamethyleneimine were injected at the same time a cooled mixture of 14.7 g (0.1 mole) of 77.09% by weight HOS (20% by weight of sulfuric acid and 2% by weight of hydroxylaminesulfate) and 26.4 g of water and 35.2 g of 30% by weight sodium hydroxide (0.264 mol at 30° to 35° C. under stirring, and after completion of injection the reaction was carried out at 30° C. under stirring for 10 minutes. After the reaction, 32.1 g of an organic layer was obtained at 30° C. As the result of GC analysis of the organic layer, the yield of N-aminohexamethyleneimine was found to be 73.1%.

What is claimed is:

1. A process for producing N-aminohexamethyleneimine which comprises reacting hexamethyleneimine with hydroxylamine-o-sulfonic acid in the presence of an aqueous solvent and an inorganic base and wherein the reaction is carried out by injecting simultaneously an aqueous solution of hydroxylamine-O-sulfonic acid and the inorganic base into an aqueous solution of hexamethyleneimine.

2. A process for producing N-aminohexamethyleneimine according to claim 1, wherein the proportion of hexamethyleneimine relative to hydroxylamine-O-sulfonic acid is 2 to 4 moles of hexamethyleneimine per 1 mole of hydroxylamine-O-sulfonic acid.

3. A process for producing N-aminohexamethyleneimine according to claim 1, wherein said aqueous solvent is water.

4. A process for producing N-aminohexamethyleneimine according to claim 3, wherein the proportion of water relative to hydroxylamine-O-sulfonic acid is 4.5 to 8 parts by weight of water quantity per 1 part by weight of hydroxylamine-O-sulfonic acid.

5. A process for producing N-aminohexamethyleneimine according to claim 1, wherein said inorganic base is selected from the group consisting of hydroxides of alkali metals and hydroxides of alkaline earth metals.

6. A process for producing N-aminohexamethyleneimine according to claim 5, wherein said inorganic base is selected from the group consisiting of sodium hydroxide, potassium hydroxide, magnesium hydroxide, calcium hydroxide and barium hydroxide.

7. A process for producing N-aminohexamethyleneimine according to claim 1, wherein an amount of said base is 1.0 to 3.0 equivalents based on the theoretical amount.

8. A process for producing N-aminohexamethyleneimine according to claim 1, wherein the reaction is carried out at a temperature of 0° to 100 ° C. for one hour.

9. A process for producing N-aminohexamethyleneimine according to claim 8, wherein the reaction is carried out at a temperature of 10° to 50 ° C. for one hour.

10. The process of claim 4, wherein the proportion of hexamethyleneimine to hydroxylamine-O-sulfonic acid is 2 to 4 moles per 1 mole respectively.

11. The process of claim 10, wherein said inorganic base is selected from the group consisting of hydroxides of alkali metals and hydroxides of alkaline earth metals.

12. The process of claim 11, wherein said inorganic base is selected from the group consisting of sodium hydroxide, potassium hydroxide, magnesium hydroxide, calcium hydroxide and barium hydroxide.

13. The process of claim 12, wherein an amount of said base is 1.0 to 3.0 equivalents based on the theoretical amount.

14. The process of claim 13, wherein the reaction is carried out at a temperature of 0° to 100° C.

15. The process of claim 14, wherein the reaction is carried out at a temperature of 10° to 50° C for one hour.

16. The process of claim 11, wherein the reaction is carried out at a temperature of 0° to 100° C.

17. The process of claim 8, wherein said aqueous solvent is water.

18. The process of claim 17, wherein the proportion of water relative to hydroxylamine-O-sulfonic acid is 4.5 to 8 parts by weight of water quantity per 1 part by weight of hydroxylamine-O-sulfonic acid.